United States Patent [19]
Bolsen

[11] Patent Number: 5,872,004
[45] Date of Patent: Feb. 16, 1999

[54] TEST PACK FOR ASSESSING THE EFFICIENCY OF A STERILIZATION PROCESS

[75] Inventor: Kathryn A. Bolsen, Mentor, Ohio

[73] Assignee: Steris Corporation, Mentor, Ohio

[21] Appl. No.: 835,406

[22] Filed: Apr. 8, 1997

[51] Int. Cl.[6] .............................. C12M 1/34; C12Q 1/22; A61L 2/20
[52] U.S. Cl. ........................... 435/287.4; 435/31; 422/28
[58] Field of Search .................................. 435/287.4, 31; 422/28

[56] References Cited

U.S. PATENT DOCUMENTS

| | | | |
|---|---|---|---|
| 5,552,320 | 9/1996 | Smith | 435/287.4 |
| 5,738,824 | 4/1998 | Pfeifer | 422/3 |
| 5,750,184 | 5/1998 | Imburgia | 427/2.13 |

OTHER PUBLICATIONS

Spicher G. et al. What should be the length and inner diameter of a test piece for microbiological testing of formaldehyde gas sterilization procedure? Zentralblatt fur Bacteriologie, Microbiologie und Hygiene, vol. 179, No. 5, pp. 457–468, 1984.

*Primary Examiner*—Sandra E. Saucier
*Assistant Examiner*—Vera Afremova
*Attorney, Agent, or Firm*—Fay, Sharpe, Beall, Fagan, Minnich & McKee

[57] ABSTRACT

A sterilization process is assessed using a test pack having a tube (16) for simulating the difficult to clean areas of instruments, such as lumens. The tube is disposed in a tray (10), and a biological indicator (30) is connected to a tube open end. Additional biological and chemical indicators (42, 24) are inserted in corresponding receiving wells or pockets (40, 22) of the tray. The test pack is covered with a porous wrapping (54) to simulate the challenge of wrapped instruments. The test pack is inserted in a sterilizer along with instruments to be sterilized. The biological indicator (30) will only register effective sterilization if sufficient sterilant flows through the length of the tube to the indicator.

18 Claims, 2 Drawing Sheets

TEST PACK FOR ASSESSING THE EFFICIENCY OF A STERILIZATION PROCESS

BACKGROUND OF THE INVENTION

The present invention relates to the sterilization and disinfection arts. It finds particular application in conjunction with the assessment of vaporized hydrogen peroxide sterilization systems, and will be described with particular reference thereto. It should be appreciated, however, that the invention is also applicable to other sterilization, disinfection, and sanitization methods.

The reusability of medical instruments has become increasingly important in an effort to provide cost effective health care. Many of the instruments that are now sterilized, such as endoscopes, contain tortuous paths, narrow lumens, and other difficult to sterilize areas. In addition, it is often preferable to sterilize medical instruments in the wrappings used to maintain the sterility of the instruments between sterilization and reuse. Such wrappings increase the difficulty of ensuring successful sterilization of the instrument.

A number of methods have been developed for assessment of sterilization processes that are employed to destroy microorganisms which were deposited on the instruments during use. Biological indicators and chemical indicators are among the techniques currently used for monitoring the effectiveness of sterilization cycles. Biological indicators contain a calibrated population of living organisms, e.g. bacterial spores, having a high resistance to the sterilization process under investigation. After exposure to the sterilization cycle, the indicator is incubated in a bacteriological nutrient media to encourage outgrowth of any remaining viable spores. Growth of microorganisms is an indication that the sterilization process has not been effective. Typically several days to a week are required for a detectable outgrowth.

Chemical indicators contain a substance that exhibits a change in a measurable property under predesignated conditions which are normally coincident with sterilization. Chemical indicators provide an instant readout, but the readout only indicates that the conditions for sterilization were met, without assuring that sterilization in fact occurred. Typically, a biological and/or chemical indicator is placed in the sterilizer, along with the instruments to be sterilized, to assess the effectiveness of the cycle.

A variety of sterilants are now available for sterilization of medical instruments. Hydrogen peroxide vapor is a particularly useful sterilant because of its effectiveness at low temperatures, which avoids degradation of heat-sensitive medical instruments. Hydrogen peroxide decomposes to water and oxygen which are not harmful to medical personnel supervising the sterilization process or to patients. Moreover, the water and oxygen by-products are environmentally safe and require no special processing for disposal.

As for other sterilants, however, medical instruments and their wrappings can provide challenges to the effectiveness of sterilization. Hydrogen peroxide vapor is normally mixed with water vapor which, at the temperatures employed for hydrogen peroxide sterilization, is not a sterilant. Moreover, water vapor permeates into wrappings and narrow lumens more readily than hydrogen peroxide vapor, reducing the effectiveness of the hydrogen peroxide sterilant. In addition, condensed water vapor shields any submerged organisms from the hydrogen peroxide. As a result, complete sterilization of the instrument may not always be effectuated. For this reason, conventional biological and chemical indicators can sometimes over-estimate the effectiveness of hydrogen peroxide sterilization processes for those medical instruments and their wrappings which encourage condensation.

The present invention provides a new and improved hydrogen peroxide sterilization evaluation system which overcomes the above referenced problems and others.

SUMMARY OF THE INVENTION

In accordance with one aspect of the present invention, a test pack for the assessment of a sterilization process is provided. The test pack includes a tray, resistant to degradation by the sterilization process and a tube, also resistant to degradation by the sterilization process. The tube has two open ends, the first open end being configured for receiving an indicator and the other for receiving sterilant gas. During the sterilization process, sterilant flows in the second open end in the tube, through the tube, and to the indicator received at the first end.

In accordance with another aspect of the present invention, a method for the assessment of a sterilization process is provided. An indicator is inserted into one end of a tube disposed in a test pack. The test pack is subjected to a gaseous sterilant sterilization cycle to be assessed. The gaseous sterilant flows into another end of the tube, through the tube, and to the biological indicator. The indicator is then removed from the test pack and the success of the gaseous sterilant reaching the indicator is assessed.

One advantage of the present invention is that it enables the effectiveness of the sterilization of instruments having wrappings or tortuous paths and lumens to be assessed.

Another advantage of the present invention is that it enables the optimal sterilization conditions for medical instruments to be determined.

Another advantage of the present invention is that a variety of chemical or biological indicators are orderly placed within the test pack.

Still further advantages reside in rapid removal from the sterilizer and simplified evaluation of the effectiveness of the sterilization process.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
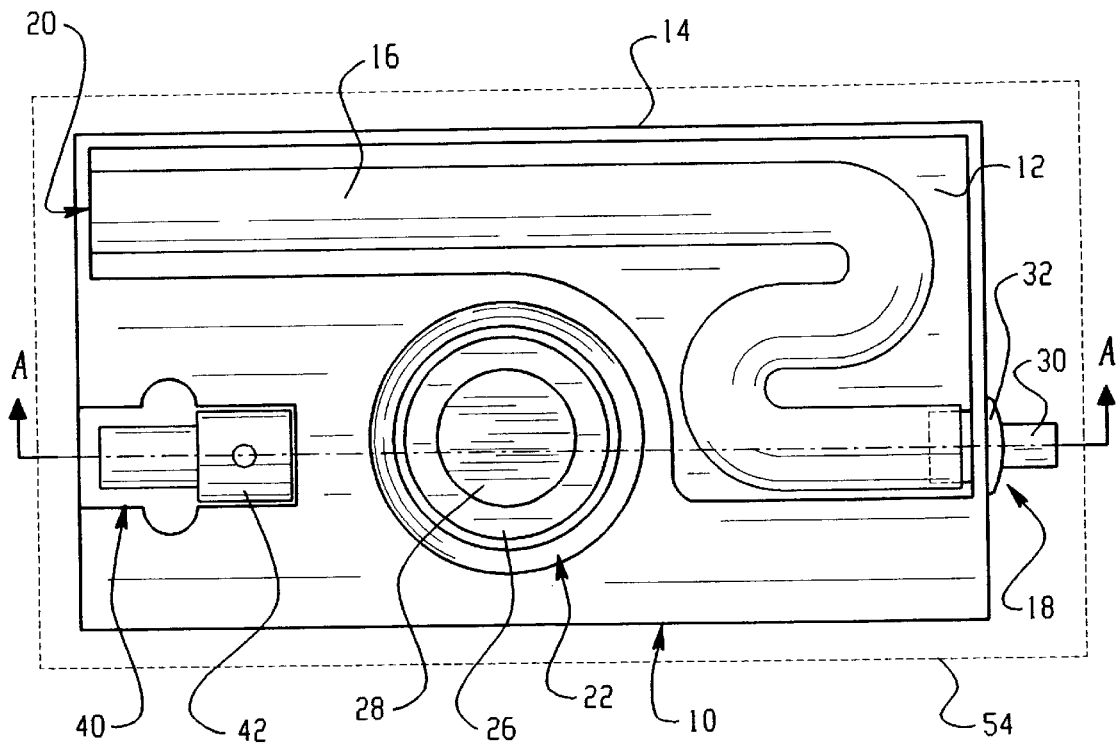
FIG. 1 is a top view a preferred embodiment of a test pack for assessing the efficiency of a sterilization process of the present invention.
Figure 2:
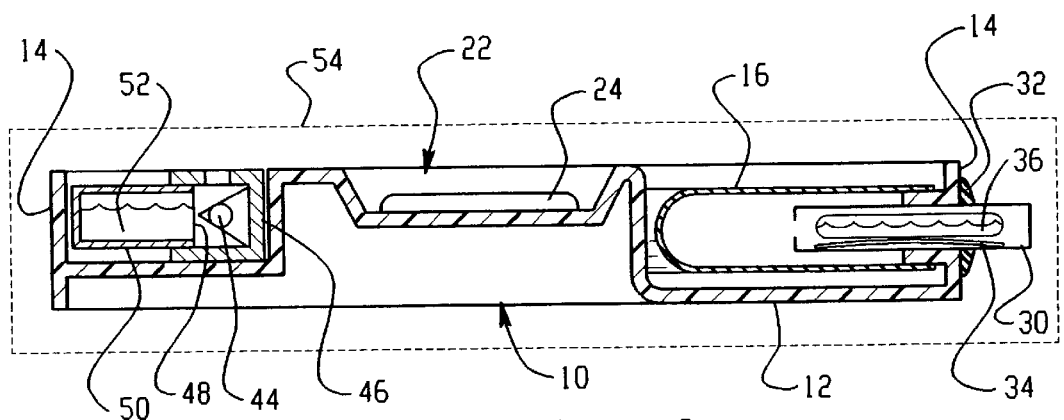
FIG. 2 is a sectional view through section A—A of FIG. 1, in combination with a biological indicator, a chemical indicator, and a self contained biological indicator.
Figure 3:
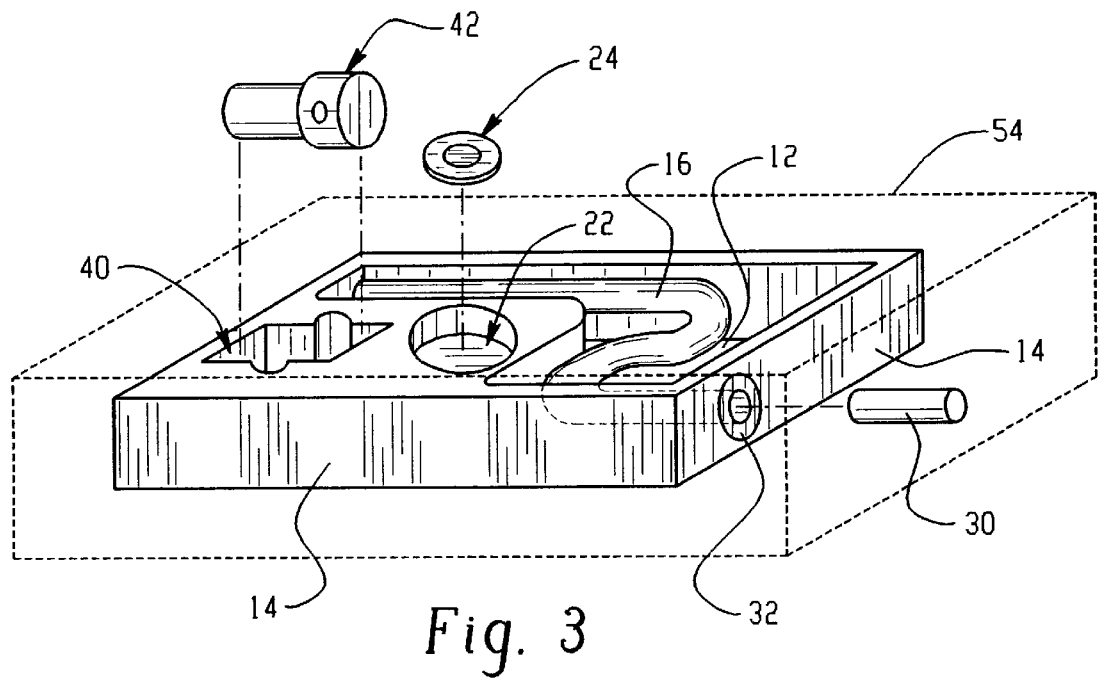
FIG. 3 illustrates an expanded, perspective view of the test pack of FIGS. 1 and 2.

With reference to FIGS. 1, 2, and 3, a tray 10 is constructed of a material that is resistant to the sterilization process, e.g. a thermoformable plastic. Optionally, the material is one which can withstand repeated sterilization cycles enabling the test pack to be reused. The tray 10 has a base 12 and vertical sides 14 connected to the base. A tube 16, having two open ends, is disposed within the tray 10. The tube 16 is constructed of a material that is resistant to the sterilization process, such as medical grade silicone. The internal diameter and length of the tube are selected to simulate challenges provided by the instruments to be sterilized. For an assessment of sterilization of typical medical instruments having lumens, a tube length of about 0.5 meters and an internal diameter of about 1–2 mm. provides a comparable challenge. The tube may be coiled or otherwise bent to simulate the instruments and to fit within the tray.

Preferably, the open ends of the tube are attached to nipples integrally formed with the tray side walls at first and second openings 18 and 20 in two of the vertical sides of the tray.

An indent or well 22 in the tray is shaped to hold a chemical indicator 24, such that the indicator can be removed from the tray following exposure to a sterilization process or observed for visible changes. The chemical indicator preferably includes a carrier 26 that is treated with a chemical substance 28 that exhibits a measurable change in a property or properties when the required conditions for sterilization have been met. Particularly preferred chemicals are those that exhibit a measurable change in a human-visible property, such as color, in relation to the exposure of the indicator to hydrogen peroxide. For example, a paper or plastic disk 26 has a region treated with a dye that changes color with exposure to hydrogen peroxide vapor, e.g., violet to clear. Each molecule of hydrogen peroxide which reaches the chemical indicator reacts with a molecule of the dye to change its color. Other chemical systems, including enzymes, which change a human or machine readable property are also contemplated.

The first opening 18 is sized to receive or connect with an indicator such as a rapid read biological indicator 30. Preferably, the indicator is inserted through the opening and into the interior of the tube 16. A locking mechanism 32, such as a silicon gasket, frictionally engages the biological indicator 30 and surrounds the opening 18. The gasket frictionally engages the indicator to hold it in position during the sterilization process and preferably allows its release afterwards for evaluation. The mechanism 32 also seals between the tube 16 and the indicator 30 to ensure that sterilant reaches the indicator only by passing along the full length of the tube and not through opening 18. The biological indicator contains a carrier strip 34 with a calibrated population of a microorganism, such as a bacterial spore, which exhibits a high resistance to the sterilization process. After sterilization, the carrier strip is immersed in a culture medium where any remaining viable organisms start to grow. Where the indicator 30 is of the self-contained variety, the culture medium 36 is within the indicator but separated from the carrier by a membrane, which membrane is broken after the sterilization process. The growth or lack of growth provides an indication of the effectiveness of sterilization. When a rapid read indicator is used, the indication of spore growth is readable within a few hours.

Optionally, a second recess or well 40 is defined in the tray 10 and is shaped and sized to receive another indicator 42 during the sterilization process. When the indicator 30 is a rapid-read biological indicator, the indicator 32 is preferably a self-contained biological indicator of the type that allows for a more accurate assessment of the effectiveness of the sterilization process, but which takes longer, e.g., several days to a week. In a preferred self-contained biological indicator, a spore carrier 44 is carried on a cap 46 adjacent a seal 48. After the sterilization cycle, the cap is pushed onto a vial 50 which (i) breaks the seal 48 and immerses the carrier in a reservoir 52 of culture medium in the vial and (ii) seals the carrier and culture medium from the atmosphere.

The test pack is also suited or adaptable to accommodate a variety of other indicators or monitors designed to evaluate sterilizer conditions during the sterilization. Use of the test pack allows for orderly insertion and removal of the indicators from the sterilizer.

After the selected indicators have been inserted in the tray 10, the tray and its contents are optionally covered with a porous wrapping 54 of the type used for covering medical instruments to maintain sterility during storage. Preferably the wrapping is impermeable to the passage of microorganisms. The wrap is manually folded around the test package and taped or clipped against unwrapping. Alternatively, a sheet of the wrap is releasably adhered over the top of the tray. The wrapped test pack is inserted in the sterilizer along with the instruments to be sterilized. During sterilization, the sterilant moves through the wrapping of the test pack and into contact with the biological indicators. However, unless the sterilant succeeds in penetrating the full length of the tube, the biological indicator 30 inserted in the tube will not be subject to the effects of the sterilant.

On completion of the sterilization process, the wrapping is removed from the test pack and the indicators removed for assessment of the effectiveness of the sterilization process.

Figure 4:
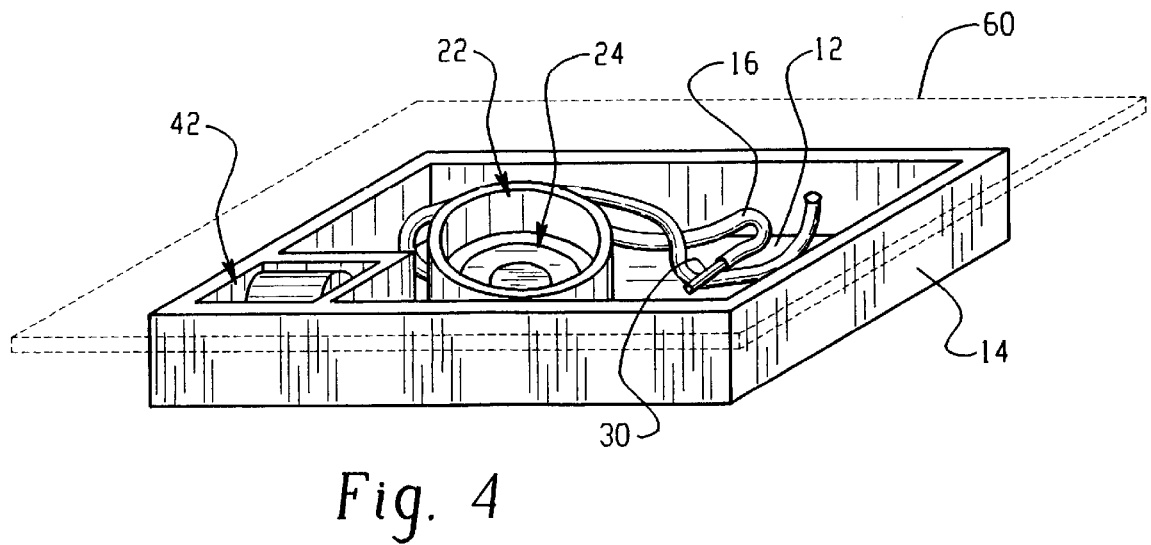
FIG. 4 is a perspective view of another preferred embodiment of a test pack for assessing the efficiency of a sterilization process in accordance with the present invention.

With reference to FIG. 4, the tray 10 optionally has a peel-off top 60 of the porous material attached to the vertical sides 14 of the tray. After the sterilization, the porous top is removed for easy removal of the chemical and biological indicators 24, 30, and 42 following the sterilization process.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A test pack for evaluating a sterilization process, the test pack comprising:
   a) a tray, resistant to degradation by a gaseous sterilant, the tray including a base and sides connected to the base, the sides including at least a side first opening for receiving an indicator; and,
   b) a tube, resistant to degradation by the gaseous sterilant, the tube being positioned in the tray and including a first end of the tube and a second end of the tube, the first end of the tube being connected with the sides around the side first opening, the first open end of the tube being configured for receiving the indicator, such that during the sterilization process, the gaseous sterilant flows in the second end of the tube, through the tube, and to the indicator received in the side first opening and the tube first end.

2. The test pack of claim 1, wherein the tray includes a well, the well shaped for holding a second indicator.

3. The test pack of claim 2, wherein the tray includes a recess, disposed within the tray, the recess being configured for holding a third indicator during sterilization.

4. The test pack of claim 1, wherein the tray includes a recess, disposed within the tray, the recess being configured for holding an additional indicator during sterilization.

5. The test pack of claim 1, wherein the indicator received at the first end of the tube is a rapid-read biological indicator, the indicator including a calibrated population of a microorganism, such as a bacterial spore, having a high resistance to the sterilization process, and including a detection system for assessing the viability of the microorganisms after the sterilization process.

6. The test pack of claim 5, further including a well in the tray holding a chemical indicator, the chemical indicator containing a chemical system having a property that undergoes a measurable change in response to preselected conditions appropriate for sterilization.

7. The test pack of claim 5 further including a recess in the tray holding an additional biological indicator, the biological indicator being one which gives an accurate assessment of sterilization, but in a longer time than for the rapid-read biological indicator and the chemical indicator.

8. The test pack of claim 1, wherein the tube has a length and an inner diameter which provides a challenge to the passage of sterilant comparable to that provided by medical instruments being sterilized in the sterilization process.

9. The test pack of claim 1, wherein the tube is about 0.5 meters long and has an inner diameter of about 1 to about 2 mm.

10. The test pack of claim 1, further including:
   a means for holding devices used to monitor sterilization conditions.

11. The test pack of claim 1, wherein the sides of the tray define a side second opening and the second end of the tube is connected with the tray side around the side second opening.

12. A test pack for evaluating a sterilization process, the test pack comprising:
   a) a tray, resistant to degradation by a gaseous sterilant, the tray being configured with a plurality of recessed pockets for receiving a plurality of indicators;
   b) a tube, resistant to degradation by the gaseous sterilant provides a challenge to the passage of sterilant, the tube being contained in the tray and including a first end and a second end, the first end of the tube being connected to the tray and configured for receiving a first of the plurality of indicators, such that during the sterilization process, the gaseous sterilant flows in the second end of the tube, through the tube, and to the first indicator received at the first end of the tube; and,
   c) a microbe impermeable, gaseous sterilant permeable porous wrapping wrapped over the tray, the wrapping covering the pockets and at least the first and a second indicator, such that the wrapping prevents microbes from reaching the indicators after sterilization and provides a gaseous sterilant passing challenge to the passage of the gaseous sterilant to the indicators during the sterilization process.

13. A test pack for evaluating a sterilization process, the test pack comprising:
   a) a tray, resistant to degradation by a gaseous sterilant, an indicator receiving opening and a gaseous sterilant receiving opening being defined in the tray;
   b) a tube, resistant to degradation by the gaseous sterilant received within the tray, the tube connected to the tray at the indicator receiving opening in the tray and including a first end and a second end, the first end of the tube being configured for receiving an indicator which is inserted through the indicator receiving opening in the tray, and the second end being in gaseous communication with the gaseous sterilant receiving opening, such that during the sterilization process, the gaseous sterilant flows in the second end of the tube, through the tube, and to the indicator received at the first end of the tube; and,
   c) a microbe impermeable, porous material covering the second end of the tube.

14. A test pack for evaluating a sterilization process, the test pack comprising:
   a) a tray, resistant to degradation by a gaseous sterilant, the tray including an opening in a wall of the tray;
   b) a tube, resistant to degradation by the gaseous sterilant, the tube positioned in the tray and including a first end and a second end, the tube being sealed adjacent the tube first end to the tray providing an access path from the second end of the tube and through the tube to an interior side of the tray opening; and,
   c) a seal member for sealing an indicator into the tray opening preventing the gaseous sterilant from entering the tube through the first end of the tube, such that during the sterilization process, the gaseous sterilant flows in the second end of the tube, through the tube, and to the indicator received in the tray opening.

15. A method for assessing a sterilization process, the method comprising:
   a) inserting a portion of an indicator into an opening in a test pack, a tube being placed in and sealed to the test pack, the tube having a first end connected to the test pack opening, such that an interior of the test pack opening and the portion of the indicator inserted into the test pack opening are accessible only through the tube from a second end of the tube;
   b) subjecting the test pack to a gaseous sterilant sterilization cycle to be assessed, the gaseous sterilant flowing into the second end of the tube, through the tube, and to the portion of the indicator inserted into the test pack opening;
   c) removing the indicator from the test pack; and,
   d) evaluating the indicator and assessing success of the gaseous sterilant reaching the indicator.

16. The method of claim 15, further including inserting a plurality of indicators into the test pack, the test pack being configured for holding a plurality of indicators.

17. The method of claim 16, further including: wrapping the test pack in a material of the type used to maintain the sterility of medical instruments after sterilization.

18. The method of claim 15 wherein the gaseous sterilant is selected from the group consisting of hydrogen peroxide vapor, peracetic acid vapor, and combinations thereof.

* * * * *